United States Patent [19]

Klostergaard

[11] Patent Number: 5,128,258
[45] Date of Patent: Jul. 7, 1992

[54] IRON-RELEASING MONOKINES

[75] Inventor: Jim Klostergaard, Kingwood, Tex.

[73] Assignee: Board of Regents, The University of Texas System, Austin, Tex.

[21] Appl. No.: 1,073

[22] Filed: Jan. 7, 1987

[51] Int. Cl.$^5$ .............. C12N 5/00; C12P 21/00; C07K 15/00; C07K 15/06
[52] U.S. Cl. ................. 435/240.2; 435/70.3; 435/70.4; 530/351
[58] Field of Search ............ 435/68, 183, 184, 803, 435/804, 70.3, 70.4, 69.5; 530/351, 837, 830; 514/2, 21; 424/85.1

[56] References Cited
PUBLICATIONS

Hibbs et al. (1984), *Biochem. Biophys. Res. Comm.*, 123:716–723 (abstract).
Dialog Search Report.
PCT International Search Report.
Klostergaard et al. (1987), *Jrnl. Biol. Resp. Mod.*, 6:313–330.
Klostergaard et al. (1987), *Chemical Abstracts*, 106(13): Abstract 100662T, p. 517.
Klostergaard et al. (1987), *Chemical Abstracts*, 106(25): Abstract 212340T, p. 521.
Klostergaard et al. (1985), *Biological Abstracts*, 80(5): Abstract 40216, p. AB-403.
Klostergaard et al. (1985), *Jrnl. Biol. Resp. Mod.*, 4:195–209.
Kilbourn, "Inhibition of the Mitochondrial Respiration of Tumor Cells by Soluble Factors Released by Activated Macrophages", Order #DA8419088, Diss. Abstr. Int. B, 1984, 45(5), 1424–25.
Kilbourn et al., "Activated macrophages secrete a soluble factor that inhibits mitochondrial respiration of tumor cells", J. Immunology, vol. 13, 2577–2581, 1984.
Drapier et al, "Murine Cytotoxic Activated Macrophages Inhibit Aconitase in Tumor Cells" J. Clin. Invest, vol. 78, 790–797, 1986.

*Primary Examiner*—John Doll
*Assistant Examiner*—Gail Poulos
*Attorney, Agent, or Firm*—Arnold, White & Durkee

[57] ABSTRACT

A substantially purified preparation containing one or more soluble Iron-Releasing Monokines and a method of preparing and using same are disclosed. The monokine is heat labile and is retained by ultrafiltration on a YM-10 membrane. Molecular exclusion chromatography of macrophage conditioned supernatant containing the monokine yields fractions in the 30,000 to 65,000 relative molecular weight range with iron-releasing activity. Kinetic studies show that the monokine is rapidly released from activated macrophages after triggering with bacterial endotoxin, reaching plateau levels within 2–4 hours. The response of cells to the monokine depends on both the dose of the monokine administered and the duration of its exposure. The Iron-Releasing Monokine is distinct from other factors secreted by activated macrophages, such as a cytolytic factor and Respiratory Inhibition Factor which causes reversible lesions in the electron transport chain.

21 Claims, 4 Drawing Sheets

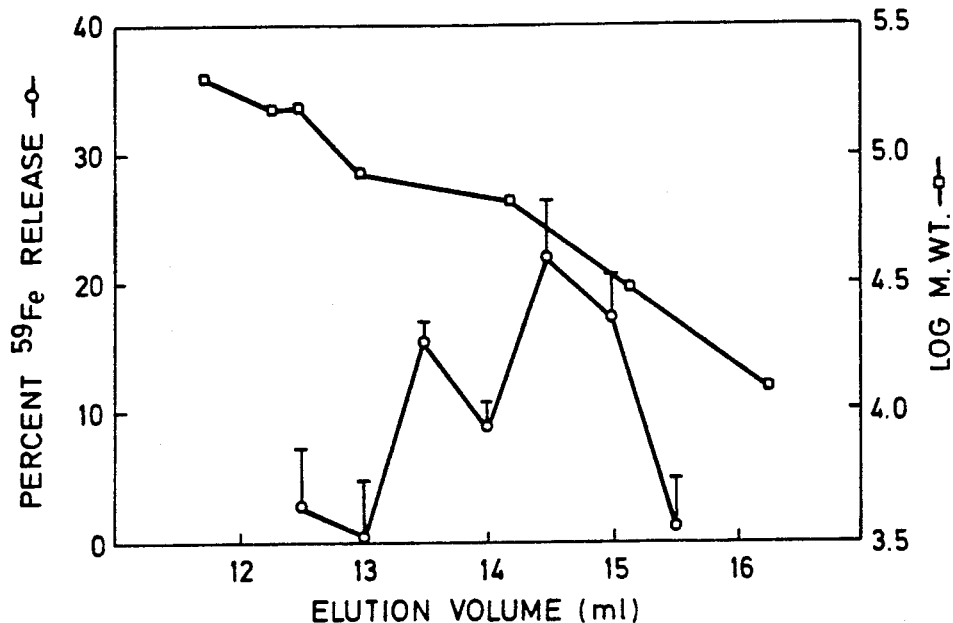
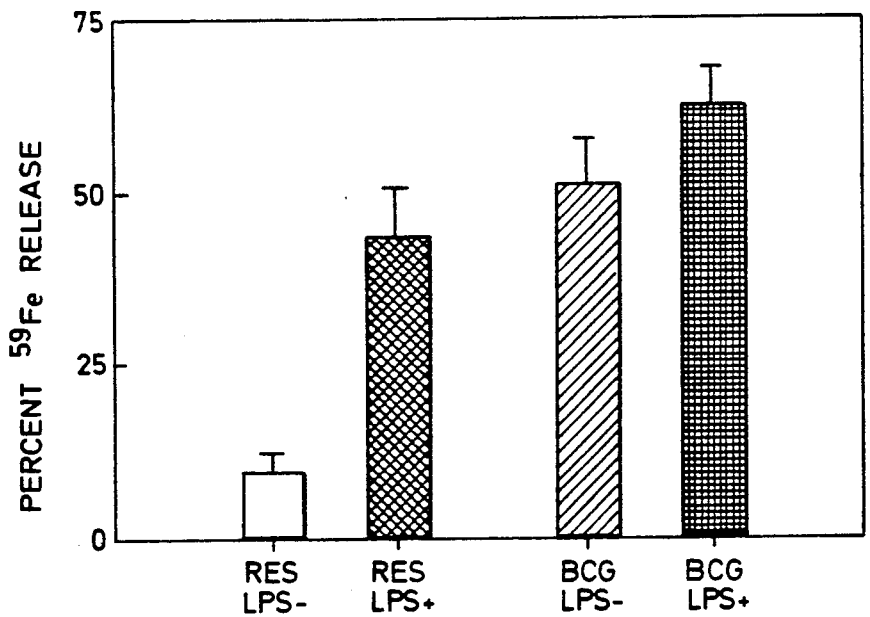

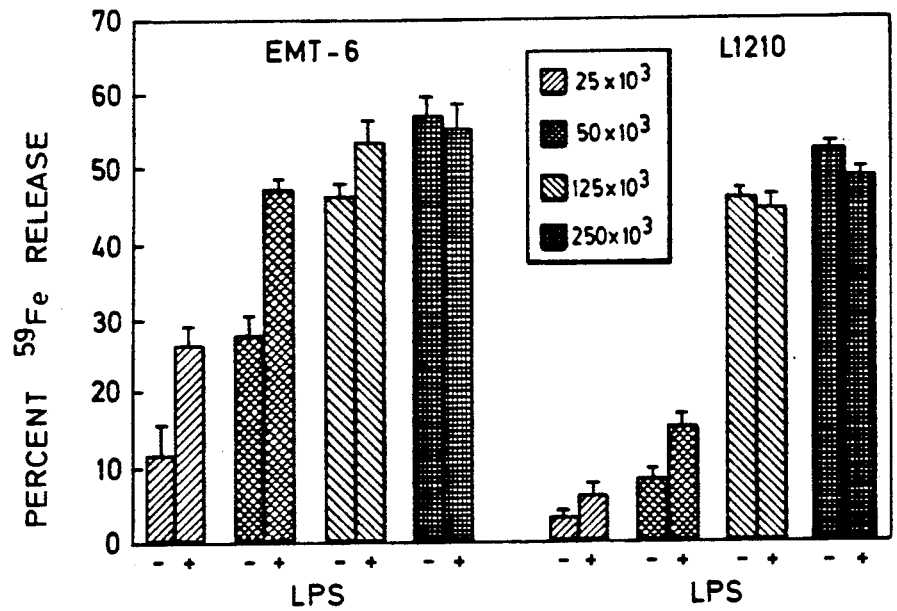
Fig. 3 EFFECT OF MØ DENSITY AND LPS TRIGGERING ON $^{59}$Fe RELEASE FROM EMT-6 AND L1210 TARGETS
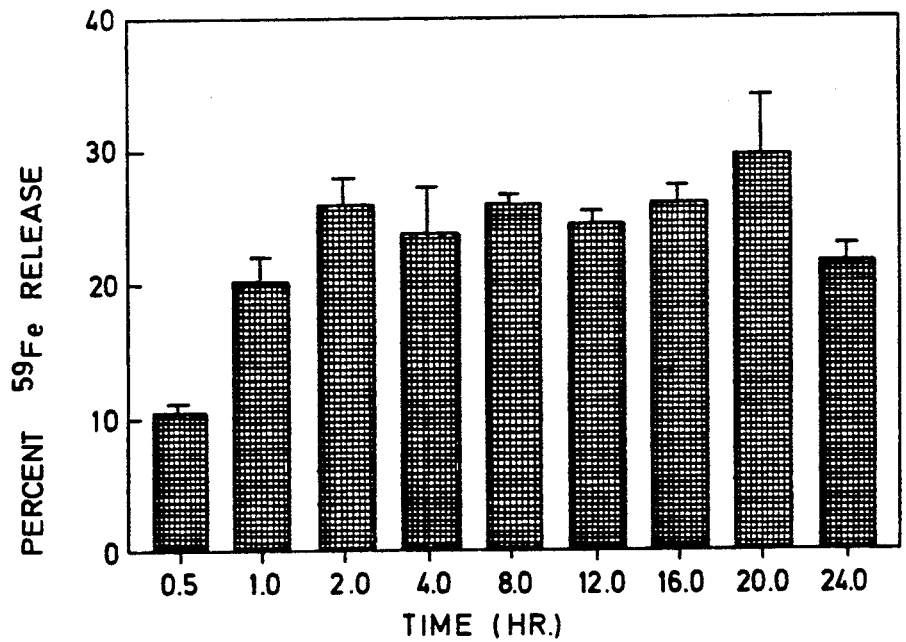
Fig. 4 KINETICS OF PRODUCTION OF Fe-RELEASING FACTOR FROM BCG-AMØ

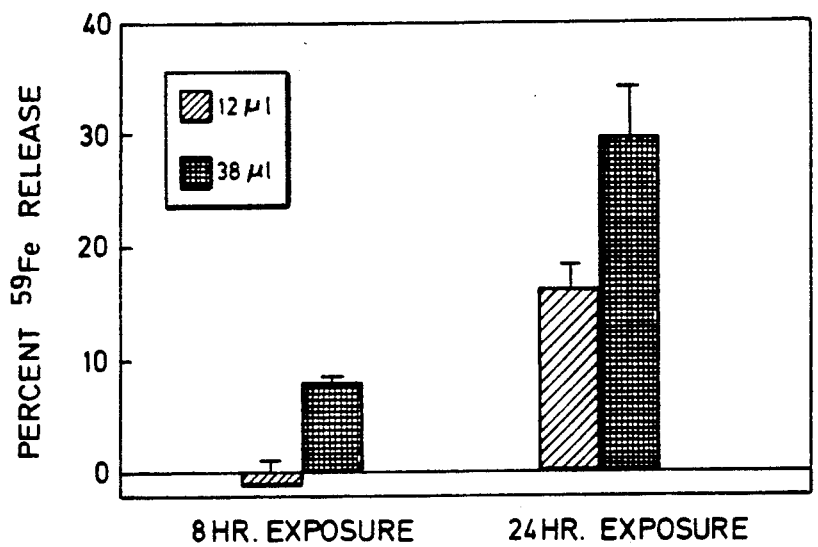
Fig. 5 EFFECT OF DOSE AND TIME OF EXPOSURE OF CS ON $^{59}Fe$ RELEASE FROM EMT-6 TARGETS
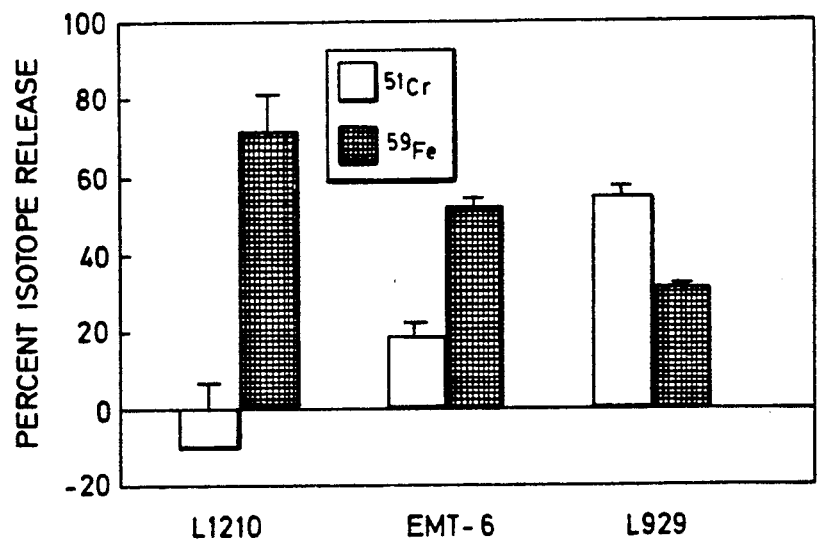
Fig. 6 TUMOR CYTOTOXICITY OF BCG-AMØ

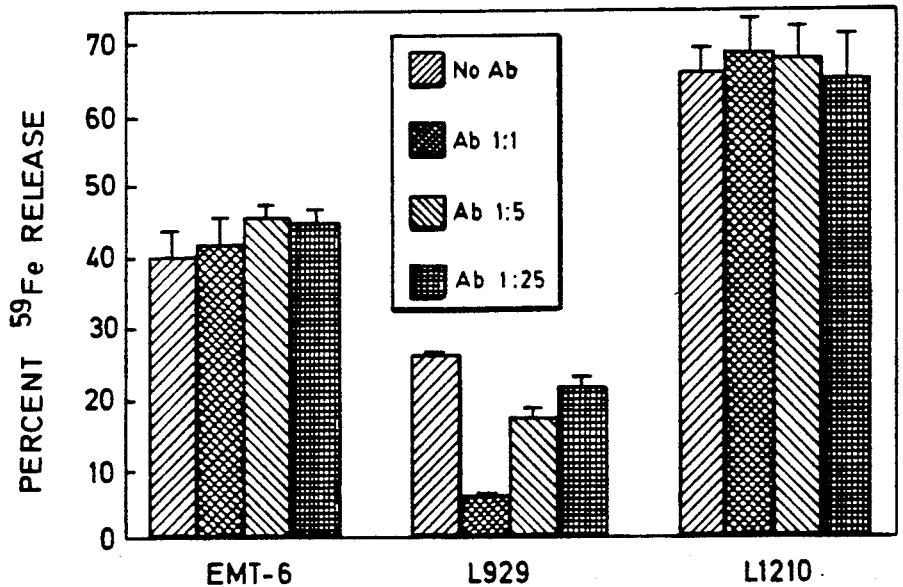
Fig. 7 EFFECT OF ANTI-NECROSIN ANTIBODY ON $^{59}Fe$ RELEASE FROM EMT-L929 AND L1210 TARGETS COCULTURED WITH BCG ACTIVATED MØ
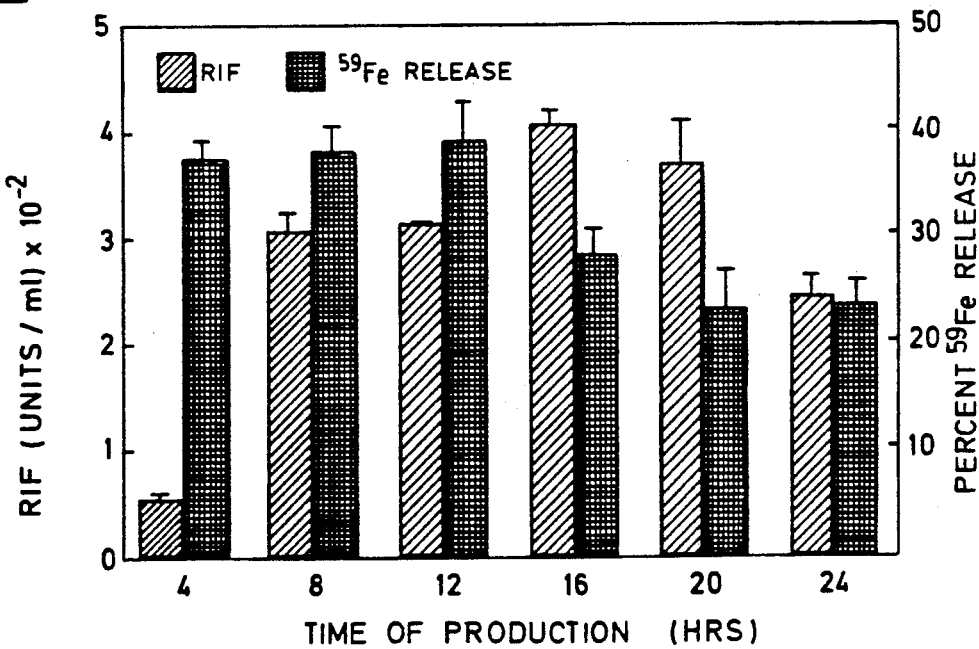
Fig. 8 KINETICS OF PRODUCTION OF RIF AND $^{59}Fe$-RELEASING ACTIVITY BY BCG ACTIVATED MØ

IRON-RELEASING MONOKINES

BACKGROUND OF THE INVENTION

This invention relates to preparations which are useful in inhibiting the proliferation of human tumor cells and more particularly is directed to macrophage derived factors which cause release of intracellular iron and thereby inhibit catalytic activity of enzymes with iron-sulfur centers.

Cancer is a very wide spread and severe health problem which affects millions of people yearly, resulting in debilitating symptoms and often death. Numerous approaches, often fruitless, have been taken by medical scientists in an attempt to identify substances which may be of some usefulness in slowing or stopping the growth of human tumors. One avenue which has shown some promise is through the stimulation of the afflicted patient's immune system, thereby inducing the patient's immune system to produce substances capable of reducing the growth rate of tumor cells or, hopefully, killing them outright. Unfortunately, such an approach is often of little use in that the immune systems of cancer patients are either over burdened already or are simply incapable of responding to such immuno-stimulation.

This has led researchers to attempt to identify and purify substances produced by the immune systems of immuno-competent animals which are active in slowing or stopping the growth rate of tumor cells. Included in such studies have been attempts to identify substances produced by "activated" macrophages, that is, macrophages which have been stimulated by some immuno-stimulating agent to produce tumor-suppressing substances. Indeed, a number of tumor-suppressive substances have been identified from activated macrophages.

Furthermore, numerous in vitro studies demonstrate that coculture of activated macrophages with tumor cells leads to cytolysis or cytostatis of the tumor cells. Although the cytolytic response has been more extensively studied, macrophage induced cytostasis is more frequently observed and is believed to play an important role in controlling the development, progression and spread of tumor cells.

One cytostatic mechanism of activated macrophages is mediated through lesions induced by the effector cell in the target cell mitochondrial electron transport chain (ETC), in particular at Complex I and II. Such lesions result in growth inhibition or, if the damaged cells are not able to conduct adequate levels of glycolysis, death of the target. Kilbourn and co-workers, (1984) *J. Immunol.*, 133:2577, have demonstrated that this cytotoxic mechanism might be accounted for by the secretion of a monokine, termed respiration inhibitory factor (RIF), which appears in large measure to mimic the activated macrophage in the exertion of cytostatic effects on a number of tumor cells.

Studies demonstrating release of intracellular iron by tumor cells provide evidence for a second pathway of macrophage-mediated cytostasis. These studies show a temporal correlation between iron release and inhibition of DNA synthesis in tumor cells cocultured with cytotoxic activated macrophages. Recently, studies by Hibbs et al., (1986), *J. Clin. Invest.*, 78:790 have demonstrated a mechanism whereby macrophage-induced iron release could affect tumor cell metabolism.

Using a macrophage-tumor cell cocultivation system, Hibbs et al. showed that macrophage induced release of intracellular iron from tumor cells was associated with inhibition of the Krebs cycle enzyme aconitase, one of a class of enzymes having an iron-sulfur center essential for catalytic activity. Activity of the enzyme was restored by culturing the injured tumor cell in a medium supplemented with ferrous iron and a reducing agent, an observation suggesting that the inhibition was mediated by removal of an iron atom from the iron-sulfur center of the enzyme. Thus, macrophage-induced iron release has been causally linked to inhibition of at least one enzyme with an iron-sulfur center. Furthermore, studies demonstrating that macrophage mediated iron release continues long after the inhibition of aconitase has been reported to be complete suggest that lesions aside from the one at aconitase may exist.

Despite the potential importance of macrophage mediated iron release as a mechanism for inducing tumor cell cytostasis, previous studies of the phenomenon have employed cytotoxic macrophage coculture systems rather then attempting to identify whether a soluble factor per se was being expressed by the macrophages.

In contrast, the present invention provides for a preparation containing a soluble factor or factors capable of mediating iron release from tumor cell targets without the need for the presence of macrophages. Since this preparation induces release of iron from tumor cells without the need for macrophage coculture, it is likely to prove important as an inhibitor of tumor cell growth.

SUMMARY OF THE INVENTION

The present invention is directed to a preparation which induces intracellular iron release, an event associated with inhibition of enzymes having an iron-sulfur center. The preparation of the present invention is likely to prove useful as an inhibitor of such enzymes and as growth inhibitor of cells requiring such enzymes. In general, the preparation includes a purified soluble factor or factors which in substantially purified form may be identified upon molecular exclusion chromatography as having a relative molecular weight of between approximately 30,000 and 65,000, the preparation being capable of causing release of intracellular iron from viable tumor cells. The preparation is derivable from macrophage-conditioned supernatant, wherein macrophage-conditioned supernatant (CS) is defined as a culture medium containing biological products produced by activated macrophages.

The invention also provides a soluble factor (or factors) for inhibiting enzymes with iron-sulfur centers and inhibiting the proliferation of tumor cells, wherein the factor is prepared by a method which includes the steps of preparing a macrophage conditioned supernatant and fractionating the supernatant into the soluble factor. In a preferred embodiment, the supernatant is subjected to ultrafiltration prior to fractionation. Fractionation of the supernatant may include, but is not limited to, one of the various forms of fractionation based on differences in molecular weight, for example, gel exclusion chromatography, high pressure liquid chromatography and the like. Further, it is contemplated that the iron-releasing factor may be purified by methods employing other forms of fractionation, such as ultracentrifugation, preparative gel electrophoresis, gel permeation chromatography or any other fractionation technique known to those of skill in the art for fractionating molecules.

In general, preparation of the macrophage conditioned supernatant includes the steps of harvesting macrophages from a mammal, incubating the macrophages in a incubation medium and separating the macrophages to provide the resultant conditioned supernatant. Any number of tissue culture media or physiologic buffers known in the art can be used as the incubation medium. Moreover, it has been found that pre-immunization of the mammal with a macrophage activator will result in the generation of even greater amounts of the factor by the subsequently harvested macrophages. A number of suitable activators are described herein, however, in a preferred embodiment Bacillus Calmette Guerin ("BCG") is utilized as the activator. Similarly, in a preferred embodiment, the mammal used is a mouse. In a further embodiment, prior to being separated from the conditioned medium, the harvested macrophages are incubated in medium to which a triggering agent, for example, bacterial endotoxin, is added. Furthermore, where the macrophages are treated in vitro with a suitable triggering agent, the in vivo activation step is not required.

Therefore, an object of the invention is to provide a method for inhibiting the proliferation of tumor cells which includes subjecting tumor cells to an effective dose of a preparation which includes the iron-releasing factor in substantially purified form. For these purposes, an effective dose is defined to be the amount of iron releasing monokine(s) present in 20 ul of conditioned supernatant produced by culturing $1 \times 10^6$ macrophages in 1 ml of culture medium. This dose of supernatant causes a 50% growth inhibition of $1 \times 10^4$ EMT-6 cells in 18–24 hours.

A further object of the invention is to provide a method for inhibiting enzymes with iron-sulfur prosthetic groups. This method includes exposing such enzymes to an effective amount of any of the embodied preparations. For these purposes an effective amount is defined as the amount of iron releasing monokine(s) present in 100 ul of conditioned supernatant produced by culturing $1 \times 10^6$ macrophages in 1 ml of culture medium. This dose causes 40–50% of $^{59}Fe$ release from EMT-6 cells in 18–24 hours.

DESCRIPTION OF THE DRAWINGS

FIG. 1—High Pressure Liquid Chromatography (HPLC) Gel Filtration of Macrophage Conditioned Supernatant (CS) with Iron-releasing Activity. CS was concentrated by ultrafiltration, and subjected to molecular sieving on Superose 12. Fractions were assayed for iron-releasing activity on EMT-6 cells (0). A calibration curve of log molecular weight vs. elution volume was established (*) to allow determination of apparent molecular weight.

FIG. 2—Requirement for Macrophage Activation to Induce Intracellular Iron Release from Cocultured EMT-6 Cells. Resident or BCG-activated macrophages were cocultured with 59Fe-prelabeled EMT-6 cells in the absence or presence of endotoxin. After 24 hr the amount of intracellular iron released was determined.

FIG. 3—Effect of Macrophage Density and Endotoxin Exposure on Intracellular Iron Release from EMT-6 and L-1210 Targets. EMT-6 ($10 \times 10^3$ per well) and L-1210 ($20 \times 10^3$ per well) targets were cocultured with BCG-activated macrophages seeded at varying densities ($25 \times 10^3$ to $250 \times 10^3$) with or without exposure to endotoxin. After 24 hr the amount of intracellular iron released was determined.

FIG. 4—Kinetics of Production and Release of Iron-releasing Monokine from BCG-activated Macrophages. Macrophages ($1 \times 10^6/2$ cm$^2$/ml) were triggered with 100 ng/ml endotoxin, and iron-releasing activity released into the supernatant was determined on prelabeled EMT-6 cells.

FIG. 5—Kinetics of Response of EMT-6 Cells to Different Doses of Iron-releasing Monokine in Macrophage Conditioned Supernatant (CS). $^{59}Fe$-prelabeled EMT-6 cells were exposed to different levels of CS for 8 or 24 hr. The extent of iron-release is shown.

FIG. 6—Release of $^{51}Cr$ and $^{59}Fe$ from Tumor Targets Cocultured with BCG-activated Macrophages. Target cells were prelabeled either with $^{51}Cr$ or $^{59}Fe$ and introduced to adherent BCG-activated macrophages; endotoxin (200 ng/ml) was added for the duration of the coculture. The conditions were as follows: L-1210, $20 \times 10^3$ targets, $250 \times 10^3$ macrophages, 22 hr assay; EMT-6, $10 \times 10^3$ targets, $250 \times 10^3$ macrophages, 22 hr assay; L-929, $25 \times 10^3$ targets, $50 \times 10^3$ macrophages, 18 hr assay.

FIG. 7—Effect of Antinecrosin Antiserum on $^{59}Fe$ Release from EMT-6, L-929 and L-1210 Targets Cocultured with BCG-Activated Macrophages. Iron-prelabeled EMT-6 ($10 \times 10^3$ per well), L-929 ($25 \times 10^3$ per well) or L-1210 ($20 \times 10^3$ per well) were cocultured with BCG-activated macrophages at 250,000, 50,000 and 250,000 macrophages per well, respectively. To parallel cultures were added 20 ul of a 1:20 dilution of antiserum in a final volume of 200 ul of medium overlaying macrophages and tumor cells. In addition, two serial 5-fold dilutions of this antiserum were added to cocultures. These represent the values 1:1, 1:5 and 1:25. After 20 hr the extent of iron release from these target cells was determined.

FIG. 8—Mediation of Respiration Inhibition and Intracellular Iron Release by Supernatants from BCG-Activated Macrophages. Samples of supernatants from BCG-activated macrophages triggered with endotoxin were obtained at various time points starting at 4 hr and up to 24 hr after triggering with endotoxin. These samples were assayed for respiration inhibitory factor and were also applied directly to iron-labeled EMT-6 cells. After 24 hr the assays were terminated and values for these supernatants in the assay for respiration inhibitory factor and the assay for induction of intracellular iron release were determined.

DESCRIPTION OF THE PREFERRED EMBODIMENTS

The present invention, in its most general and overall scope, is directed to methods and compositions for inhibiting enzymes with iron-sulfur centers and is believed to be useful for inhibiting tumor cell growth and proliferation. Compositions of the invention are generally defined as including an iron releasing monokine (or monokines) identifiable upon molecular exclusion chromatography as having a relative molecular weight between 30,000 and 65,000, the factor being capable of causing the release of intracellular iron by viable tumor cells. The iron-releasing monokine is isolatable from the supernatant of activated macrophages.

The factor of the present invention is distinct from other factors produced by activated macrophages. For example, BCG-initiated macrophages triggered with endotoxin produce a soluble factor, termed Cytolytic Factor which causes the lysis of murine and human tumor cells in vitro in 24 to 72 hours. This factor, which can be extensively purified by conventional molecular sieving, anion exchange chromatography and hydroxyapatite chromatography, has a molecular weight of approximately 150,000 Daltons. Cylolytic Factor is inhibited with serine proteases and is serologically related to tumor necrosis factor.

Activated macrophages also produce a Respiration Inhibitory Factor (RIF) associated with reversible lesions in the election transport chain. This factor is described by Kilbourn et al (1984), J. Immunol., 133:2577.

The soluble factor (or factors) of the present invention functions by causing the release of intracellular iron, an event associated with inhibition of enzymes requiring iron for catalytic activity. Numerous enzymes contain "essential" iron-sulfur centers and thus are all considered possible target enzymes. For example, the Krebs cycle enzyme aconitase, the oxidoreductases of Complex I, II and III of the electron transport chain, and ribonucleotide reductase, the enzyme which catalyzes the rate limiting step for DNA synthesis, all contain ironsulfur centers essential for their catalytic activity. Since inhibition of such enzymes would affect important metabolic pathways for the tumor cell, a molecule capable of mediating such inhibition could be used to inhibit growth of tumor cells.

Preparation of the factor or factors of the present invention generally involves several steps. The first step involves the preparation of a supernatant derived from cultures of activated macrophages. Although not mandatory, the macrophages to be cultured are generally first activated in vivo by injecting a mammal (a mouse is preferred, but other mammals such as guinea pigs, hamsters, rats, rabbits, etc., may be used) with an effective amount of a macrophage activator. BCG is a preferred activator, but other agents known to induce cytotoxic activation of macrophages may be used as well. These compounds include, but are not limited to, Immunotone (American Biotechnology Co.), C. Parvum, supernatant derived from mitogen stimulated murine T-cells, gamma-interferon and muramyl dipeptide. Of course, the amount of activator administered will vary with the particular activator used, but in general, an effective amount is that amount required to produce cytotoxic macrophages, recognizable by established criteria. More particularly, when BCG is used, a dose of approximately $2 \times 10^7$ colony forming units is the preferred dose. Intraperitoneal administration is preferred. Any regimen of injection sufficient to induce activation of the macrophages in vivo may be used, however, in a preferred embodiment, the mammals are first injected with the activator 25 days before the macrophages are harvested, then "boosted" with a second dose 4 days before harvest. Furthermore, it should be appreciated that in vivo activation is not strictly required where the macrophages are sufficiently activated in vitro as described below.

After the in vivo activation step, if such a step is employed, the macrophages are harvested from the host mammal by peritoneal lavage. This technique generally involves injecting the peritoneal cavity of the animal with a liquid medium, such as a physiologic buffer, massaging the peritoneal area, and draining the peritoneal exudate from the animal. At this stage, the peritoneal exudate contains a mixture of cell types, including the activated macrophages. The cell mixture may be enriched for the activated macrophages by any of a number of methods known to separate macrophages from contaminating cell types. These include, but are not limited to: treating the mixture which includes the contaminants with specific antibodies and complement; and allowing the macrophages to adhere to a solid support such as a tissue culture dish, and washing away non-adherent contaminants. In a preferred embodiment of the present invention, the macrophages are selected by culturing them in serum free medium in a plastic tissue culture dish, allowing them to adhere to the plastic, and washing away non-adherent contaminants. This procedure yields a population which is approximately 90% pure. The macrophages may then be precultured in any of a number of suitable culture media. Such media are well known to those skilled in the art.

In general, in order to obtain optimal production of iron-releasing factor, the macrophages should be treated with a triggering agent shortly after they are established in culture. In a preferred embodiment, the triggering agent is endotoxin derived from E. coli, however it will be appreciated that other agents, such as other bacterial endotoxins, muramyl dipeptide, phorbol mysistate acetate, calcium ionophore A23187, tuftsin, and poly I-C, may be used as triggering agents. In fact, it should be noted that where the macrophages have been sufficiently activated in vivo, this step may be omitted entirely.

Production of macrophage conditioned supernatant is generally completed after four to twelve hours of culture. Since macrophages triggered with endotoxin as described above have been shown to produce the iron-releasing factor or factors almost immediately after triggering, and since the factor is detectable in cultures incubated up to at least 24 hrs., shorter or longer incubation times may be used. However, four to twelve hours is considered optimal. At any rate, at the termination of the selected incubation period, the resultant conditioned supernatant is removed from the culture. It may then be stored at $-20°$ C. until needed for further use. The growth inhibitory action of the iron-releasing monokine containing supernatant can be titered by a colorimetric assay described by Green et al. (1984), J. Immunol. Methods, 70:257, incorporated herein by reference. It has generally been found that 20 ul. of conditioned supernatant produced by culturing $1 \times 10^6$ macrophages in 1 ml of culture medium is effective to provide a 50% growth inhibition of $10 \times 10^3$ EMT-6 cells in 18-24 hours.

Of course, the advantages of the present invention are realized by identification and separation of a soluble iron-releasing monokine(s) having a relative molecular weight between 30,000 and 65,000 from the macrophage conditioned supernatant. The iron-releasing monokine(s) may be identified and separated by any of a number of selection techniques known to those skilled in the art of separating biological molecules. These techniques include, but are not limited to, selective ultrafiltration, ultracentrifugation, preparative gel electrophoresis, molecular exclusion chromatography, ion exchange chromatography and the like. However, a preferred method for separating and identifying the monokine(s) entails clarification of the conditioned supernatant by centrifugation, followed by ultrafiltration and subsequent HPLC gel filtration.

More specifically, the ultrafiltration step involves placing the conditioned supernatant in a stirred cell apparatus pressurized with nitrogen. The apparatus contains a membrane which retains only molecules above a specified molecular weight. Several membranes are commercially available and may be used for practicing the invention; however, a YM-10 membrane, which retains molecules with a molecular weight greater than 10,000, is preferred. Using this ultrafiltration protocol, the conditioned supernatant containing the iron-releasing monokine(s) is concentrated approximately six-fold.

As previously noted, further purification of the iron-releasing monokine(s) can be achieved by a number of techniques. However, in a preferred embodiment, the concentrated supernatant is chromatographed on a gel filtration column. Numerous gels suitable for such chromatography are known by those skilled in the art of chromatography. These include, but are not limited to, agarose gels, Sepharose gels, Sephadex gels, Sephacryl gels, and polyacrylamide gels. However, an HPLC Superose 12 gel filtration column is preferred. The column may be equilibrated with any suitable equilibration solution; however, Dulbecco's phosphate buffered saline is preferred. Fractions eluting from the column in the same volume with molecular weight standards ranging from 30,000 to 65,000 are a particularly preferred source of the monokine(s).

The purified iron-releasing monokine(s) may be formulated into a number of preparations suitable for treatment of tumor patients or suitable for use as enzyme inhibitors. The monokine may be formulated into such preparations in neutral or salt forms. Pharmaceutically acceptable salts, include the acid addition salts (formed with the free amino groups of the monokine(s)) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In general, the monokine(s) may be admixed with any vehicle in which it retains function. Of course, selection of the proper vehicle will depend on the manner in which the monokine(s) will be used. In general, suitable vehicles include aqueous solutions, saline, dextrose, glycerol and the like, or combinations thereof.

Obviously, any preparation of the monokine to be used in human tumor therapy must be formulated with a nontoxic excipient. In theory, any of a number of pharmaceutical excipients may be used, so long as the factor retains its function when it is administered in the presence of such excipient. The factor may be administered by any of a number of techniques known to those skilled the art of administering biologic compounds. Such techniques include, but are not limited to, intravenous injection, subcutaneous injection, intraperitoneal injection, and continuous infusion. Furthermore, it is contemplated that the factor could be administered in conjunction with other chemotherapeutic agents known to those skilled in the art.

In addition, the iron releasing monokine(s) may be used to inhibit enzymes with iron-sulfur centers. For example, it is believed that the factor will prove useful in producing inhibition of the Krebs cycle enzyme aconitase. Thus, the factor might be used to block the aconitase-mediated conversion of citrate to isocitrate. Numerous uses for other enzyme inhibitors, including class-specific and enzyme-specific inhibitors, are known in the art. It is contemplated that the iron-releasing monokine(s) of the present invention may be similarly employed where the desired effect requires inhibition of enzymes with an iron-sulfur center. For example, the monokines could be used in a diagnostic kit.

The following examples demonstrate methods for preparing, assaying, and characterizing the iron-releasing monokines. Of course, alternative, and possibly more effective modes for practicing the invention may be determined in the future. The examples are simply meant to demonstrate the best mode for practicing the invention known to the inventor at the present time.

EXAMPLE I

Preparation of Iron Releasing Monokine(s)

A. Preparation of BCG-Activated Macrophages

BCG-activated macrophages produced according to the protocol described below were used to study the mechanism of activated macrophage induction of intracellular iron release. They were also used to prepare conditioned supernatant from which the iron-releasing monokine(s) was purified.

1. Animals

Six- to eight-week old male CD-1 mice were obtained from the University of Texas, Science Park, Bastrop, Tex. Ten- to twelve-week old male CB6F1 mice (Balb-/cAnN x C57B1/6N) were provided through the breeding program of the Department of Tumor Biology, The University of Texas M.D. Anderson Hospital and Tumor Institute, Houston, Tex.

2. Preparation of BCG-Activated Macrophages

Macrophage monolayers were obtained by peritoneal lavage of mice that had been injected i.p. with $2 \times 10^7$ colony forming units of BCG (Trudeau Institute, Saranac Lake, N.Y.), 25 and 4 days before harvest. The peritoneal exudate cells were suspended in $Ca^{++}$- and $Mg^{++}$-free phosphate buffered saline (PBS), collected by centrifugation, adjusted to the proper density ($1-2 \times 10^6$ cells/ml) and then allowed to adhere to plastic for 4 hr in serum-free culture medium at 37° C. After this time, non-adherent cells were removed by washing with PBS. Remaining cells were judged to be >90% macrophages by morphological and functional criteria. These cells were then utilized either in cocultures with radiolabeled tumor cells to determine cytotoxicity or iron release, or for supernatant production.

B. Purification of Iron-Releasing Monokine From Macrophage Conditioned Supernatant The following procedures were performed in order to purify the iron-releasing monokine and determine its approximate molecular weight. Murine macrophages were seeded at $25 \times 10^6$ per 100 mm tissue culture dish. After 4 hr of adherence, the macrophages were washed, recultured in 30 ml of DME/F-12 medium, and triggered for 2-6 hrs phenol-extracted *E. coli* serotype 0.28; B12, Sigma Chemical Co., St. Louis, Mo.). The resultant conditioned supernatant was collected and frozen at −20° C. until further use.

The conditioned supernatant was thawed and clarified by centrifugation. It was then applied to an ultrafiltration apparatus (Millipore Corp., Danver, Mass.) and subjected to concentration under N2 on a YM-10 membrane which retains molecules having a molecular weight greater than 10,000 Daltons. Samples of starting supernatant, effluent and retentate were collected and assayed for iron-releasing activity. The results of this experiment, shown in Table 1, demonstrated that the iron-releasing activity was retained by the membrane.

TABLE 1

TM-10 Ultrafiltration of Iron-Releasing Monokine

| Fraction assayed[1] | Volume assayed (ul) | Percent $^{59}$Fe-Release[2] |
|---|---|---|
| Unfactionated conditioned supernatant | 12 | 15.6 ± 5.9 |
| Retentate | 4 | 3.7 ± 2.0 |
|  | 12 | 34.6 ± 3.3 |
|  | 38 | 48.9 ± 2.0 |
| Effluent | 4 | 2.6 ± 2.6 |
|  | 12 | 0.0 ± 0.4 |
|  | 38 | −1.5 ± 3.9 |

[1] Macrophage conditioned supernatant was subjected to ultrafiltration on a YM-10 membrane under N2; after concentration to one-sixth the initial volume, both the retentate and effluent were assayed for iron-releasing activity.
[2] 1 × 10$^4$EMT-6 cells which had been prelabeled with $^{59}$Fe were seeded in microwells in 200 ul medium. After 2 hr, the supernatant fractions were added to the targets and $^{59}$Fe release was determined 22-24 hr later.

In order to further characterize the factor in terms of molecular weight and to demonstrate the further purification of the factor(s) by molecular weight fractionation, 250 ul of a 10-20 X concentrated retentate was injected onto an HPLC gel filtration column (Superose 12, Pharmacia, Piscataway, N.J.). This column was equilibrated with Dulbecco's phosphate buffered saline. 500 ul fractions were collected and replicates of two different volumes were assayed on iron-labeled EMT-6 cells, seeded at 10,000 cells/well in 200 ul volume in a 96 well plate and preincubated for 2 hrs at 37° C. Twenty hours after the test fractions from the column were added to the cells, the iron-releasing activity of each fraction was determined by measuring $^{59}$Fe release as described in Example II, C.

An approximate relative molecular weight for the iron-releasing monokine was then determined using a standard calibration curve log of molecular weight versus elution volume. The following molecular weight standards were used: blue dextran, −2×10$^6$d, 7.75 ml; beta amalase, −2×10$^5$d, 11.75 ml; IgG - 1.5×10$^5$d, 12.25 ml; transferring, 85×10$^3$d, 13.0 ml; hemoglobin, 64×10$^3$d, 14.25 ml; carbonic anhydrase, 29×10$^3$d, 15.25 ml; and cytochrome C, 12×10$^3$d, 16.25 ml.

The results of this procedure, shown in FIG. 1, demonstrated that the iron-releasing activity migrated as a poorly resolved doublet with an approximate relative molecular weight in the range of 30,000 to 65,000. The highest amount of activity eluted at a volume consistent with a relative molecular weight of roughly 50,000.

C. Purification of Other Monokines From Macrophage Conditioned Supernatant

The following protocols were employed to prepare purified preparations of Cytolytic Factor and Respiration Inhibitory Factor (RIF). The factors thus prepared are compared with the iron-releasing monokines in Example IV.

Conditioned supernatant containing Cytolytic Factor and Respiration Inhibitory Factor was obtained by culturing of 25×10$^6$ BCG-activated macrophages, triggered with 100 mg/ml of endotoxin, on a 100 mm tissue culture dish (Corning Glassworks) in 30 ml of DME/F-12 medium supplemented with the effluent components from ultrafiltration of fetal calf serum (FCS) under nitrogen on a YM-10 membrane using a stirred cell apparatus (Amicon Corp., Danvers, Mass.).

After 18 hrs, the cultures were terminated and the resultant conditioned supernatant was harvested and concentrated on a YM-10 membrane in a stirred cell apparatus. The retentate was then subjected to molecular sieving on Sephacryl S-200 (Pharmacia, Uppsala, Sweden) in a 2.5×50 cm Econocolumn (BioRad, Richmond, Calif.) equilibrated with Dulbecco's PBS. Two ml fractions were collected at a flow rate of −30 cm/hr.

Fractions were assayed for Cytolytic Factor by employing actinomycin-D treated L-929 targets as described by Kilbourn et al., (1984) *J. Immunol.*, 133:2577 and incorporated herein by reference. One unit of lytic activity was described as that which would reduce the optical density in wells from incorporation of neutral red in treated targets to 50% of the control value when targets were seeded at 15,000 per well. A pool of cytolytic factor was harvested in the 150 kD range, and was adjusted to a specific activity of 10×10$^3$ lytic units/ml.

Fractions containing RIF were assayed by a colormetric assay. Cytolytic Factor-resistant EMT-6 cells were seeded at 5×10$^3$/100 ul/well in 96-well plates. After an overnight incubation, fractions obtained by molecular sieving were titered on these targets. After 18-24 hr, a 1:10 dilution of 5 mg MTT (Sigma) was added. The MTT-formazan that was produced after 30 minutes was determined after resolubilization with acidified isopropanol and SDS by using a Titertek Multiscan (Flow Laboratories, Rockville, Md.) and determining absorbance at 570 nm. One unit of respiration inhibitory factor activity was defined as that which would reduce the amount of MTT-formazan produced to 50% of the difference between that produced in control cultures and that produced by maximally suppressed cultures. This assay has been shown to be sensitive to both the cytostatic and respiration inhibitory effects of respiration inhibitory factor. The activity of the respiration inhibitory factor obtained from fractions in the 55-80 kD range was adjusted to 2-3×10$^3$ units/ml.

EXAMPLE II

Assays for Macrophage Induced Cytolysis and Iron Release

A. Cell Lines

The murine tumorigenic fibroblast-like line L-929 was obtained from American Type Culture Collection, Rockville, Md. The murine mammary adenocarcinoma, EMT-6, and lymphoblastic leukemia, L-1210, were obtained through the courtesy of Dr. Gabriel Lopez-Berestein, Department of Clinical Immunology and Biological Therapy, M. D. Anderson Hospital.

B. Direct Macrophage-mediated Cytolysis and Iron Release

1. $^{51}$Cr and $^{59}$Fe Release Assays

Tumor cells were prelabeled either with $^{51}$Cr, to measure subsequent cytolysis, or with $^{59}$Fe, to assess perturbation of intracellular iron pools. For chromium labeling, EMT-6, L-929 or L-1210 cells were labeled as single cell suspensions with sodium chromate (ICN, Irvine, Calif.) in 50 ml polypropylene tubes (Corning Glassworks, Corning, N.Y.). 2-5×10$^6$ targets were exposed to 50 uCi of $^{51}$Cr in 200 ul volume for 1 hr. After extensive washing these targets were added to the macrophages.

For iron labeling the targets were prelabeled with $^{59}$Fe (ferrous citrate, ICN) by overnight exposure of 0.5 (EMT-6), 1.5 (L-929) or 1.0 (L-1210)×10$^6$ cells to 1-2 uCi/ml 59Fe in 10 ml DME/F-12 medium, which was made from powder (GIBCO, Grand Island, NY). After overnight incubation, the adherent cells were trypsinized with trypsin-EDTA, and then adherent and suspension cells were washed repeatedly with media to remove non-incorporated radioisotope.

Chromium- or iron-labeled targets were added to macrophages which had been established in microwells of 96 well plates (Costar, Cambridge, MA). For EMT-6 and L-1210 targets, 250,000 macrophages were seeded per well, and for the L-929 targets, 50,000 macrophages were seeded per well. Final volume was 200 ul of tissue culture medium (DME/F-12) prepared from endotoxin-screened water and endotoxin-screened fetal calf serum (FCS; Dutchland, Denver, Pa.). Endotoxin was added at a concentration of 100–200 ng/ml. Cytotoxicity expressed by macrophages against these labeled target cells was evaluated at 18 for the L-929 cell and at 22 hr in the case of EMT-6 and L-1210 cells.

At the termination of the assay, radioactive isotope found in the culture supernatant was measured. For the adherent target cells, the supernatants were harvested directly; in the case of the L-1210 cultures, the supernatants were first rendered cell free by centrifugation. Each supernatant was subjected to analysis in a Beckman Gamma 8000 (Beckman Instruments, Fullerton, Calif.). Total release of either isotope was determined by counting the appropriate volume of the target cell suspension used for seeding initially. Spontaneous release was measured in cultures of target cells with no macrophages. Percent cytotoxicity was calculated by the following expression:

$$\% \text{ cytotoxicity} = \frac{\text{experimental release} - \text{spontaneous release}}{\text{total release} - \text{spontaneous release}} \times 100$$

2. Intracellular Iron Release Induced by Coculture of Target Cells With Activated Macrophages.

To demonstrate that activated macrophages were capable of inducing iron release from tumor cell targets, resident or BCG-activated macrophages were cocultured with $^{59}$Fe prelabelled EMT-6 cells, in the absence or presence of endotoxin. After 24 hr the amount of intracellular iron released was determined. As shown by FIG. 2, coculture of EMT-6 cells with resident macrophages only resulted in low level (approximately 10%) release of intracellular iron. Release was significantly raised by the introduction of endotoxin into the coculture (approximately 40%). In contrast, BCG-activated macrophages induced higher levels of iron release either without (approximately 50%) or with (approximately 65%) the introduction of endotoxin. This data suggests that the extent of intracellular iron release in tumor cells parallels the state of activation of the effector cells.

3. Effect of Macrophage Density and Endotoxin Exposure on Intracellular Iron Release from EMT-6 and L-1210 Targets EMT-6 and L-1210 targets were cocultured with BCG-activated macrophages at varying densities ($25$–$50 \times 10^3$ cells/well) with or without exposure to endotoxin. As seen in FIG. 3, for both target cells the extent of iron release was directly related to the density of effector cells in the microtiter well. Furthermore, the augmentation afforded by the introduction of endotoxin was only apparent at the lower macrophage densities and was substantially overridden at the higher densities. This observation probably reflects the increased frequency of cytotoxic interactions between tumor cells and activated macrophages at the higher densities.

C. Monokine-mediated $^{59}$Fe Release From Tumor Targets

The following experiment was performed in order to establish that activated macrophages induce intracellular iron release from tumor cell targets through the activity of a soluble factor. EMT-6 cells were prelabeled with $^{59}$Fe as described above; after washing, the trypsinized targets were seeded at 10,000 per well in 200 ul volume in a 96 well plate. Target cells in one set of wells were cocultured with BCG-activated, endotoxin-triggered macrophages, as described above. Targets in the second set of wells were incubated for 2 hr at 37° C, then received 100 ul of conditioned supernatant harvested from a 4 hr culture of $1 \times 10^6$ BCG-activated, endotoxin-triggered macrophages in 1 ml DME/F-12 with 10% fetal calf serum. The amount of $^{59}$Fe released into the supernatant by each set of EMT-6 targets was evaluated after 22 hrs of incubation. Percent cytotoxicity was calculated as described above. The results of this experiment showed significant iron release from cells treated with macrophage conditioned supernatant (37%) or cocultured with BMG-activated macrophages (47%).

EXAMPLE III

Characteristics of Iron-Releasing Monokine

A. Kinetics of Production of Iron-Releasing Monokine by BCG-activated Macrophages The following experiment was performed in order to determine the rate at which activated macrophages released iron-releasing monokine into the culture medium. $1 \times 10^6$ BCG-activated macrophages were seeded in 2 cm$^2$ wells of 24well plates (Costar); after 4 hr of adherence, the cells were washed with Ca$^{++}$- and Mg$^{++}$-free PBS, and then were overlayed with 1 ml medium with 10% FCS. The macrophages were triggered with 100 ng/ml of endotoxin, and supernatants were collected at intervals thereafter. The supernatants were frozen at $-20°$ C. The samples were thawed and assayed for $^{59}$Fe-releasing activity on EMT-6 targets cells. As shown by FIG. 4, the iron-releasing activity was rapidly released after the macrophages were triggered with plateau levels being reached between 2–4 hr post triggering.

B. Dose Response and Kinetics of Response of EMT-6 Cells to Iron-Releasing Monokine Iron-labeled EMT-6 target cells were established in microwells and 12 ul or 38 ul of BCG-activated macrophage conditioned supernatant, which contained iron-releasing monokine, was added to these targets. The extent of isotope release was evaluated 8 and 24 hrs after introduction of the conditioned supernatant to the target cells. As seen in FIG. 5, at the 8 hr time point, intracellular iron-release (approximately 8%) was detected only with the higher dose of the conditioned supernatant; by 24 hrs this dose caused an even more extensive iron-release (approximately 30%) at which time the lower dose also had detectable effects on mediating isotope release (approximately 15%). Although the precise mechanism responsible for the enhanced release observed on prolonged incubation remains to be elucidated, it is believed to reflect the development of lesions in iron-sulfur prosthetic groups of additional targets or more extensive destruction of the same iron-sulfur centers. Alternatively, there may be a hierarchy of iron-sulfur centers, in which case the iron-releasing monokine(s) may affect the most susceptible ones first, with the more resistant enzymes being affected only later in the incubation.

C. Heat Lability of Iron-Releasing Monokine

In order to determine its sensitivity to heat, BCG-activated conditioned supernatant containing iron-releasing monokine(s) was tested according to the following protocol: macrophage conditioned supernatant was prepared by seeding $25 \times 10^6$ BCG-activated macrophages on a 100 mm dish. After a 4 hr adherence step, the macrophages were washed and recultured in 30 ml of DME/F12 medium with 10% FCS. The cells were triggered with 100 ng/ml endotoxin and the resultant supernatant was collected 6 hrs later and stored at $-20°$ C.

At the time of assay, the supernatant was thawed and aliquoted into two batches. One batch was incubated in a water bath at 95° C. for 10 minutes, then returned to ambient temperature; the other batch received no treatment. Twelve microliter aliquotes from each batch were then added to microwells containing $10 \times 10^3$ 59-Fe labeled EMT-6 cells in 200 ul medium, the EMT-6 targets having been pre-incubated in the medium for 2 hrs prior to addition of the supernatant to be tested. Twenty-two to twenty-four hours after addition of the supernatant, $^{59}$Fe release was measured as described in Example II. The results of this experiment indicated that the iron-releasing activity was destroyed by the heat treatment. Samples receiving untreated supernatant had significant $^{59}$Fe-release ($15.6 \pm 5.9\%$) while those receiving heat treatment had no iron release ($-5.7 \pm 1.1\%$).

EXAMPLE IV

Differentiation of Iron-Releasing Monokines From Cytolytic Factor or RIF

Results obtained from the following experiments demonstrated that iron-releasing monokine(s) is distinct from both Cylolytic Factor and RIF. Thus, the iron-releasing monokine(s) is capable of being isolated in a preparation substantially free of those two factors.

A. Inability of Purified Cytolytic Factor and Respiration Inhibitory Factor to Mediate Release of Intracellular Iron EMT-6 targets were prelabeled with $^{59}$Fe and seeded in wells of microwell plates. One set of wells contained BCG-activated macrophage monolayers; a second set contained medium supplemented with unfractionated conditioned medium from BCG-activated macrophages, purified cytolytic factor or purified respiration inhibitory factor. As shown in Table 2, tumor cells incubated with BCG-activated macrophages or unfractionated CS released significant amounts of $^{59}$Fe, while those treated with cytolytic factor or respiration inhibitory factor did not.

TABLE 2

| Release of $^{59}$Fe from EMT-6 Targets | |
|---|---|
| Treatment | Percent Release |
| Mɸ[a] | 47.1 ± 1.2 |
| CS[b] | 37.5 ± 1.8 |
| CF[c] | 0.8 ± 0.5 |

TABLE 2-continued

| Release of $^{59}$Fe from EMT-6 Targets | |
|---|---|
| Treatment | Percent Release |
| RIF[d] | 0.9 ± 1.4 |

[a] $250 \times 10^3$ BCG activated macropages were triggered with 200 ng/ml endotoxin and cocultured with $10 \times 10^3$ $^{59}$Fe-labeled EMT-6 cells for 22 hrs; isotope released into the supernatant was then enumerated.
[b] 100 ul of conditioned supernatant (CS) from 4 hr culture of $1 \times 10^6$ BCG-activated Mɸ in 1 ml DME/F-12 with 10% fetal calf serum. 200 ug/ml endotoxin: $^{59}$Fe release evaluated after 22 hrs.
[c] Cytolytic factor (CF) was prepared by molecular sieving of BCG-activated macrophage CS on Sephacryl S-200; fractions in the 150 kD range which were lytic for the actinomycin D-treated L929 cell were pooled and adjusted to $10 \times 10^3$ lytic units/ml; 100 ul of the pool was added to 200 ul of $^{59}$Fe-labeled EMT-6 cells and isotope release was evaluated 22 hrs later.
[d] Respiration inhibitory factor (RIF) was prepared by molecular sieving of BCG-activated macrophage CS on Sephacryl S-200; fractions in the 55-80 kD range which caused cytostasis and mitochondrial respiration inhibition in EMT-6 cells were pooled and adjusted to $2-3 \times 10^3$ units/ml of MTT formazan inhibition activity; 100 ul of this pool was added to 200 ul of $^{59}$Fe-labeled EMT-6 cells, and isotope release was evaluated 22 hrs later.

B. Lack of Correlation Between Iron-Release and Cytolysis in Tumor Cells Cocultured With Activated Macrophages L-1210, EMT-6, or L-929 targets were labeled with either $^{51}$Cr or $^{59}$Fe; after washing, these targets were added directly to activated macrophage monolayers established in microwells. Endotoxin was added to trigger the cytotoxicity of the macrophages. At the termination of the coculture, the extent of release of either radioisotope was evaluated. As seen in FIG. 6, the L-1210 target was extremely resistant to cytolysis ($^{51}$Cr release) by BCG-activated macrophages, but released a significant portion (approximately 70%) of its intracellular $^{59}$Fe during the same time period. EMT-6 target cells showed a similar pattern of response, although the resistance to cytolysis was incomplete (approximately 15% $^{51}$Cr release). L-929 targets showed a different response in which the extent of chromium release (approximately 55%) significantly exceeded the extent of iron release (approximately 25%).

In a second series of experiments, iron labeled EMT-6, L-1210, and L-929 target cells were cocultivated with BCG-activated macrophages in a medium to which a specific antiserum raised against homogeneous necrosin had been added. This antiserum cross-reacts with, and thereby inhibits, Cytolytic Factor released by BCG-activated macrophages. As seen in FIG. 7, no inhibition of the intracellular iron release from EMT-6 and L-1210 target cells was observed over a dose range of antiserum.

In contrast, the extent of intracellular iron release from L-929 target cells appeared to be inhibited in a dosedependent manner by the introduction of the antiserum. However, this finding could be explained by the fact that fewer L-929 targets are lysed in the presence of antiserum. When L-929 target cells were labeled with $^{51}$Cr or $^{59}$Fe and cocultured with activated macrophages, introduction of different levels of anti-necrosin antiserum resulted in the blocking of the cytolytic effects of activated macrophages in a dose-dependent manner; reduction of cytolysis from approximately 60% in the absence of antiserum to approximately 20% with the highest levels of antiserum was achieved. A similar reduction in the extent of iron release was observed. Iron release was suppressed to approximately 5% compared to approximately 25% observed with the nonantiserum treated control.

Thus, two lines of evidence presented in this section indicate that macrophage induced intracellular iron release and tumor cell cytolysis are mediated through distinct mechanisms. First, cells resistant to cytolysis are sensitive to the iron-releasing activity. Second, antibodymediated inhibition of Cytolytic Factor does not inhibit iron-release in at least two of three of cell types tested.

C. Kinetic Differences Between Appearance of Respiration Inhibitory Factor and Iron Releasing Activity Samples of supernatants from BCG-activated macrophages triggered with endotoxin were obtained at various intervals up to 24 hrs after initiation of triggering. With a colormetric assay, these samples were tested for their ability to cause respiration inhibition by inflicting lesions in the electron transport chain of the mitochondria of EMT-6 target cells. In addition, their ability to mediate intracellular iron release from labeled EMT-6 target cells was determined.

As seen in FIG. 8, supernatants collected 4 hr after triggering the BCG-activated macrophages have low levels of Respiration Inhibitory Factor; however, these supernatants are capable of causing high levels of release of intracellular iron (approximately 40%). Supernatants collected at later times further reflect the disparity between Respiration Inhibitory Factor activity and iron-releasing monokine, since the latter activity appears to start to decline 12 hrs after triggering, whereas Respiration Inhibitory Factor activity appears to plateau between 16-20 hrs after triggering. These data further suggest that Respiration Inhibitory Factor and iron-releasing monokine are distinct molecules.

As noted above, the present invention has been disclosed in terms of examples considered by the inventor to be the preferred embodiments for practicing the invention. However, they are in no way meant to be the only modes for practicing this invention. For example, although the conditioned supernatant is fractioned by molecular exclusion chromatography, other methods of fractioning the supernatant are contemplated. For example, other fractionation methods which employ a molecular sizing or molecular weight fractionation can be employed. Such separation might therefore involve gel electrophoresis, ultracentrifugation or any other separation technique based on differences in molecular size or weight. Similarly, although the macrophages employed herein are murine macrophages, there in no reason why other mammalian macrophages cannot be similarly employed. Additionally, although the macrophages of the present invention are initiated using BCG and activated using *E. coli* bacterial endotoxin, there is no reason why other initiators such as lymphokines and other activators such as other bacterial endotoxins, cannot be utilized to gain the advantages of the present invention. These and all other changes should be considered within the scope of the appended claims.

What is claimed is:

1. A composition comprising a purified soluble factor characterized as follows:
    (a) identifiable upon molecular exclusion chromatography as having a relative molecular weight of approximately 30,000 to 65,000 kilodaltons;
    (b) isolatable from macrophage conditioned supernatant;
    (c) capable of causing release of intracellular iron from EMT-6 or L1210 cells in the presence of antibodies directed against necrosin;
    (d) sensitive to incubation at 95° C. for 10 minutes; and
    (e) less than about 10 units RIF activity as measured against EMT-6 cells and an iron releasing activity of about 40% iron release against said cells, when the factor is comprised in an aqueous volume of about 100 ul.

2. A soluble purified iron releasing factor prepared by a method comprising the steps of:
    (a) preparing a macrophage conditioned supernatant wherein 100 ul of the supernatant exhibits an iron releasing factor activity of about 40% iron release as measured against EMT-6 cells while exhibiting less than about 10 units RIF activity; and
    (b) fractioning the supernatant to provide a fraction which includes the soluble factor characterized as exhibiting a molecular weight upon molecular exclusion chromatography of between about 30,000 and 65,000 Daltons and capable of causing release of intracellular iron from tumor cells.

3. The factor of claim 2 wherein preparing the macrophage conditioned supernatant comprises the steps of:
    (a) harvesting macrophages from a mammal;
    (b) incubating the macrophages in a physiologic culture medium for less than about 8 hours to produce the macrophage conditioned supernatant;
    (c) collecting the macrophage conditioned supernatant.

4. The factor of claim 3 wherein the mammal is a mouse.

5. The factor of claim 3 wherein the mammal is injected with a macrophage activator before the macrophages are harvested.

6. The factor of claim 5 wherein the macrophage activator is BCG.

7. The factor of claim 3, 4, 5 or 6 wherein the physiologic culture medium comprises a triggering agent that is effective to stimulate the release of the iron releasing factor into said physiologic culture medium.

8. The factor of claim 7 wherein the triggering agent is bacterial endotoxin.

9. The factor of claim 2 wherein fractionating the supernatant comprises:
    (a) subjecting the supernatant to molecular weight fractionation; and
    (b) selecting the soluble factor by assaying fractions for iron releasing activity.

10. The factor of claim 2 wherein fractionating the supernatant comprises:
    (a) separating the supernatant into an effluent and a filtrate by ultrafiltration;
    (b) collecting the filtrate;
    (c) subjecting the filtrate to further molecular weight fractionation; and
    (d) selecting the soluble factor by assaying fractions for iron releasing activity.

11. A method for inhibiting the proliferation of tumor cells comprising subjecting the tumor cells to a dose of the preparation of claim 1 or 2 that is effective to inhibit the proliferation of said cells.

12. A method for inhibiting the activity of enzymes having iron-sulfur centers comprising exposing the enzymes to an amount of the preparation of claims 1 or 2 that is effective to inhibit the activity of said enzymes.

13. A method of preparing a soluble iron releasing factor capable of inhibiting the activity of enzymes having an iron sulfur prosthetic group, the method comprising the steps of:
   (a) preparing a macrophage conditioned supernatant which comprises iron releasing activity and less than about 100 units RIF activity/ml; and
   (b) fractioning the supernatant into a fraction which includes the soluble factor in a purified form relative to another fraction or fractions, the factor exhibiting a molecular weight of approximately 30,000 to 65,000 Daltons and capable of inhibiting the activity of enzymes having an iron prosthetic group in the presence of antibodies against necrosin.

14. The method of claim 13 wherein preparing the macrophage conditioned supernatant comprises the steps:
   (a) harvesting macrophages from a mammal;
   (b) incubating the macrophages in a physiologic culture medium to produce a conditioned supernatant; and
   (c) collecting the conditioned supernatant.

15. The method of claim 14 wherein the mammal is a mouse.

16. The method of claim 14 wherein the mammal is injected with a macrophage activator before the macrophage are harvested.

17. The method of claim 16 wherein the activator is BCG.

18. The method of claim 14, 15, 16 or 17 wherein the physiologic culture medium comprises a triggering agent that is effective to stimulate the release of the iron releasing factor into said physiologic culture medium.

19. The method of claim 18 wherein the triggering agent is bacterial endotoxin.

20. The method of claim 13 wherein fractionating the supernatant comprises:
   (a) subjecting the supernatant to gel exclusion chromatographing;
   (b) identifying the soluble factor by assaying chromatography fractions for iron releasing activity; and
   (c) selecting the soluble factor.

21. The method of claim 13 wherein fractionating the supernatant comprises:
   (a) separating the supernatant into an effluent and a filtrate by ultrafiltration;
   (b) collecting the filtrate;
   (c) subjecting the filtrate to molecular exclusion chromatography; and
   (d) selecting the soluble factor by assaying chromatography fractions for iron releasing activity.

* * * * *

UNITED STATES PATENT AND TRADEMARK OFFICE
CERTIFICATE OF CORRECTION

PATENT NO. : 5,128,258
DATED : July 7, 1992
INVENTOR(S) : Jim Klostergaard

It is certified that error appears in the above-indentified patent and that said Letters Patent is hereby corrected as shown below:

Column 18, lines 2 and 3, claim 16, "macrophage" should be -- macrophages--.

Signed and Sealed this

Twenty-fourth Day of August, 1993

Attest:

BRUCE LEHMAN

*Attesting Officer*  *Commissioner of Patents and Trademarks*